United States Patent [19]
Leight et al.

[11] Patent Number: 6,006,857
[45] Date of Patent: Dec. 28, 1999

[54] EARPLUG WITH INSERTION STEM

[75] Inventors: Howard S. Leight, Malibu; Jim Tiemens, Laguna Nigel, both of Calif.

[73] Assignee: Howard Leight Industries, San Diego, Calif.

[21] Appl. No.: 09/075,141

[22] Filed: May 8, 1998

[51] Int. Cl.[6] .................................................... A61B 7/02
[52] U.S. Cl. .......................................... 181/135; 128/864
[58] Field of Search ..................... 181/130, 135, 181/129, 131, 137; 128/864, 865, 866, 867; 2/209

[56] References Cited

U.S. PATENT DOCUMENTS

| | | | |
|---|---|---|---|
| 4,434,794 | 3/1984 | Leight | 128/864 |
| 5,249,309 | 10/1993 | Berg et al. | 128/865 |
| 5,792,998 | 8/1998 | Gardner, Jr. et al. | 181/135 |

*Primary Examiner*—Khanh Dang
*Attorney, Agent, or Firm*—Leon Rosen; Art Freilich; Robert Hornbaker

[57] ABSTRACT

An earplug is provided, of a type that includes a soft shell (12) and an insertion stem (16), which facilitates pullout of the earplug from the ear canal and which has an increased ability to block noise. The earplug includes a body or shell of soft elastomeric material with a forward portion (20) constructed to enter the ear canal and a rearward portion (22) which flares in a rearward direction. A stem (16) of more rigid material than the shell, extends along most of the length of a passage (14) formed within the shell. The shell passage has a neck part (42) at the rear of the shell forward portion. The stem has a forward flange (32) lying in interference fit within the passage at a location forward of the passage neck part, and the stem has a rearward flange (34) that lies in interference fit with the flared rear portion of the shell.

9 Claims, 2 Drawing Sheets

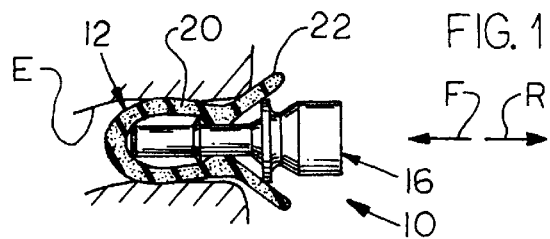
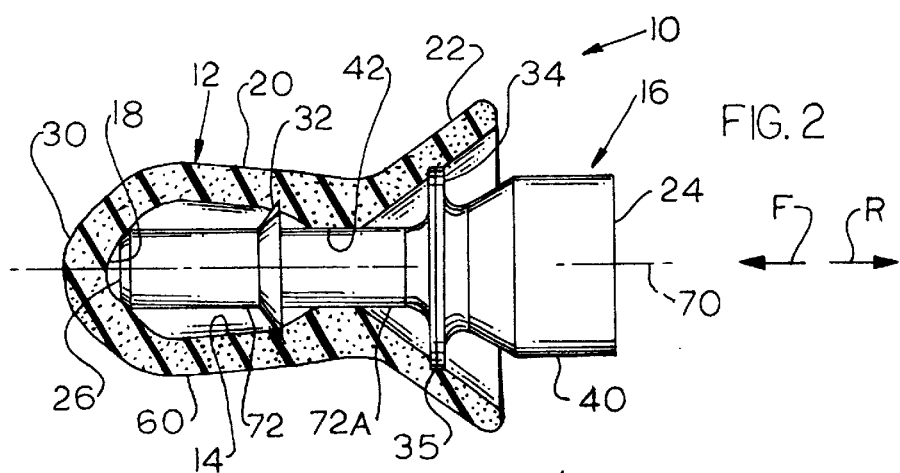
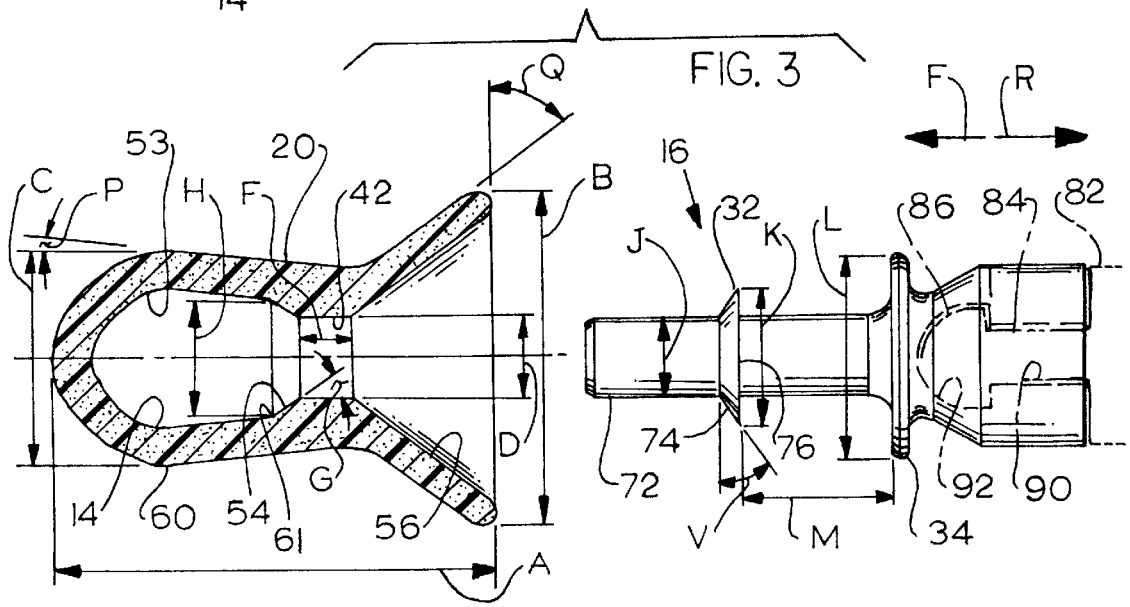

EARPLUG WITH INSERTION STEM

BACKGROUND OF THE INVENTION

One type of earplug, described in U.S. Pat. No. 4,434,794, includes a body in the form of a shell of elastomeric foam material, and a stem of more rigid material than the body, the stem extending through a passage formed by the shell. To insert the front portion of the earplug into the ear canal, the stem is pushed forward to thereby push the body forward. However, to withdraw the earplug, a person must grasp the rear of the body itself and pull it out. Applicant presently makes an earplug of the general type described in the above patent, which has a relatively high noise-blocking ability of SNR28 (European noise rating system) and NRR26 (ANSI or American National Standards Institute), with an attenuation of 26.3 db at 125 Hz. It would be desirable if the entire earplug could be more readily removed, especially in applications where the earplug lies at the end of a band that extends about halfway around the ear canal, so that separation of the ends of the bands results in the earplugs being pulled out of the ear canals of a person. Any simple change which increased noise-blocking ability would be desirable.

SUMMARY OF THE INVENTION

In accordance with one embodiment of the present invention, an earplug is provided, of a type that includes a shell of soft material and an insertion stem of more rigid material which extends along the passage formed within the shell, which facilitates pullout of the earplug and which is found to provide enhanced noise blocking ability. The shell is formed so its passage has a neck part of smallest diameter. The stem is formed with a front flange which lies forward of the neck part in the fully inserted stem position and which has a larger diameter than the neck part. As a result, pullout of the stem results in pullout of the shell from the wearer's ear canal.

The stem also has a rearward flange which lies rearward of the neck part of the shell passage. The two flanges substantially fix the location of the stem within the shell. The rear flange has a diameter at least 80% as great as the maximum diameter of the shell front portion, and is found to further block noise from passing into the person's ear canal, resulting in a higher noise-blocking rating for the earplug.

When the earplug is mounted at an end of a band that extends about halfway around a person's head, the presence of the forward flange results in the earplug automatically pulling out of the ear canal when the band ends are spread apart. The stem is preferably formed of elastomeric material and has a stem passage at its rear end, the stem passage having an undercut. The band end is formed with a projection having an enlarged head that fits into the undercut to hold the stem to the band end.

The novel features of the invention are set forth with particularity in the appended claims. The invention will be best understood from the following description when read in conjunction with the accompanying drawings.

BRIEF DESCRIPTION OF THE DRAWINGS

FIG. 1 is a sectional view of an earplug constructed in accordance with the present invention, shown fully installed in the ear canal of a person.

FIG. 2 is a sectional view similar to that of FIG. 1, showing the earplug prior to insertion in an ear canal.

FIG. 3 is an exploded sectional view of the earplug of FIG. 2.

DESCRIPTION OF THE PREFERRED EMBODIMENTS

Figure 4:
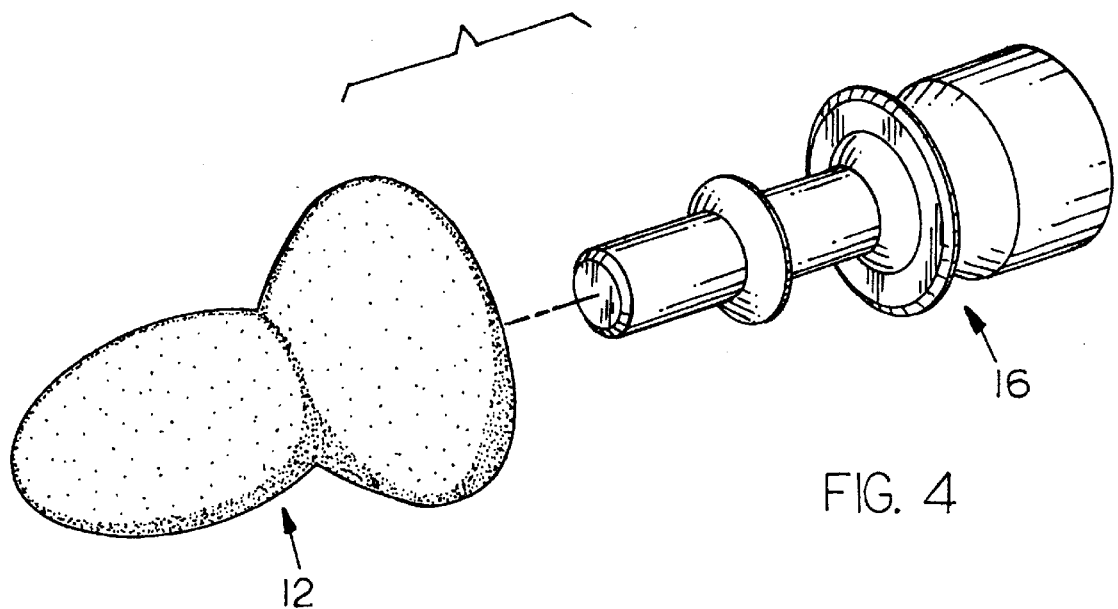
FIG. 4 is an exploded isometric view of the earplug of FIG. 2.

FIG. 2 shows an earplug 10 of the present invention, which includes a body 12 in the form of a shell with a shell passage 14 extending along most of the length of the shell to a passage forward end 18. The earplug also includes a stem 16 that extends along most of the length of the shell passage 14. The shell 12 is formed of soft, resilient, and preferably elastomeric material. It has a forward portion 20 that is designed to be received in the ear canal E of a person as shown in FIG. 1. The shell also includes a rear portion 22 that is flared in a rearward direction R, in that it has progressively greater diameters at progressively more rearward locations therealong. To insert the earplug in a person's ear canal, the person presses forwardly F against the rear end 24 of the stem. The stem has a front end 26 that preferably can engage a closed front end 30 of the shell, to push the shell into the ear canal. It may be noted that the stem includes forward and rearward flanges 32, 34 that lie in interference fit with the shell and which also can push against the shell to help push it into the ear canal.

To remove the earplug from the ear canal, a person can grasp a knob 40 near the rear of the stem and pull it. The forward flange 32 then pulls rearwardly against the shell to pull it out of the ear canal.

FIG. 3 shows that the passage 14 (and the shell outside) includes a neck part, or reduced-diameter location 42, which lies at the rear of the shell forward portion 20. A tapered passage part 54 extends forwardly from the neck part, and the shell passage has an enlarged part 53 that lies forward of the tapered part 54 and that is of larger diameter than the tapered part. The shell passage has a rear portion 56 which is tapered to match its flared outer surface, and has an open rear end.

The stem forward flange 32 is of larger diameter than the diameter of the neck part 42 of the shell passage. As a result, after the forward flange 32 is forcefully inserted through the neck part 42, the forward flange is "trapped" in place. When the stem is pulled rearwardly, the forward flange 32 pulls the shell rearwardly to pull it out of the ear canal. The largest diameter location 60 on the outside of the shell forward portion 20 lies forward of where the forward flange 32 engages the shell, so when the shell is pulled rearwardly, it "drags" the earplug body or shell behind it. Applicant constructs the forward flange 32 so it presses against the tapered passage part 54, and preferably at a location 61 at about the front end thereof. With the forward flange 32 lying at the front end of the tapered passage part 54, the front end 26 of the stem lies about in contact with the front end 30 of the shell. The forward flange 32 can slide slightly forward during push-in of the earplug into the ear canal, in which case the front end 26 of the stem pushes against the front end of the stem to push it into position. The stem has a shaft 72 with a cylindrical shaft part 72A that can slide within the neck part 42.

The rear flange 34 preferably presses against the inside of the shell rear portion 22, as shown in FIG. 2, at a location 35. This helps to provide a stable position for the stem with respect to the shell. Applicant has found that the presence of the rear flange 34, whose diameter is greater than that of the forward flange 32, and whose diameter is at least about 80% and preferably at least 90% of the largest forward location 60 of the shell front portion, results in increased noise blocking. Tests have shown that, compared to a similar earplug without the rear flange 34, the noise-blocking capability of the earplug with the rear flange 34 as specified below increased the overall noise attenuation capacity of the earplug. The noise attenuation is usually lowest at low frequencies such as 125 Hz., so attenuation at those frequencies is especially important. Applicant believes that the rear flange blocks the passage of noise that otherwise would pass through its location and around the forward flange 32 into the ear canal.

The results of actual tests on the earplug with rear flange 34 as specified, which is identified as "QBIHYG", and on an earplug of the type described in U.S. Pat. No. 4,434,794 that applicant has manufactured and which is identified as "QD", are listed below in Table I. The table shows that at the lowest attenuation frequency (at 125 Hz for both earplugs) the attenuation was increased by 4.9 db. Although the attenuation at 2000 Hz, 3150 Hz and 6300 Hz was slightly less for the QBIHYG earplug, the attenuation is already very high at these frequencies so a slight decrease is not as important as the large increase in attenuation at lower frequencies (e.g. 125 to 1000 Hz).

Figure 5:
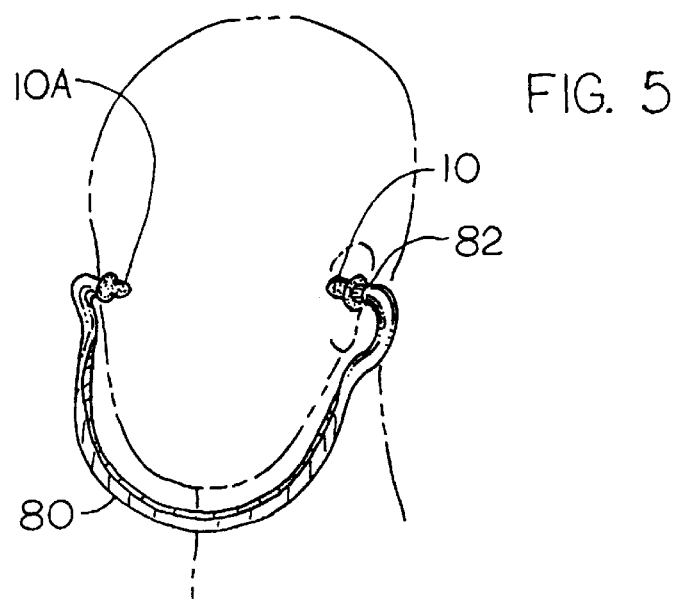
FIG. 5 is an isometric view of a banded hearing protector which includes earplugs of the type shown in FIG. 2.

FIG. 5 shows how the earplug 10 can be mounted, along with another earplug 10A, at the ends 82 of a headband 80 that fits about halfway around the head of a person. The band pushes the earplugs or pods 10 towards each other to keep them in the ears of the person. The ends 82 of the band are constructed for easy mounting on the earplugs. As shown in FIG. 3, the band end 82 includes a projection 84 with an enlarged forward end or head 86. The stem 16 is constructed with a corresponding stem passage 90 that has an undercut 92. The projection 82 can be forced through the stem passage until the head 86 lies in the undercut or stem passage enlargement 92 and thereafter remains securely in place. The fact that the stem is formed of elastomeric material and the head 86 has a tapered front end, facilitates such insertion. When a person wishes to remove the headband, he pulls apart the ends 82, causing automatic withdrawal of the earplugs or pods 10, 10A from his ear canals.

Thus, the invention provides an earplug or a headband with such earplugs forming pods, which facilitates their use, and which applicant has found to increase the noise-blocking, or attenuation, ability of the earplug. The earplug includes a body or shell of soft resilient material and a stem extending along most of the length of a passage formed within the shell. The shell passage has a neck part and the

TABLE I

| | FREQUENCY-Hz | | | | | | | | |
|---|---|---|---|---|---|---|---|---|---|
| | 125 | 250 | 500 | 1000 | 2000 | 3150 | 4000 | 6300 | 8000 |
| QD EARPLUG | 26.3 | 29.0 | 28.7 | 31.2 | 36.3 | 44.0 | 45.1 | 49.1 | 47.2 |
| QBIHYG EARPLUG | 31.2 | 31.5 | 31.6 | 32.3 | 35.1 | 42.6 | 45.8 | 47.0 | 48.0 |
| CHANGE | 4.8 | 2.5 | 2.8 | 1.1 | -1.2 | -1.4 | 0.7 | -2.1 | 0.8 |

Applicant constructs the body shell 12 of a resilient foam material having a softness or shore of about 25. Applicant constructs the stem 16 of solid elastomeric material having a shore hardness of about 50. Both the shell and the stem are symmetric about an axis 70.

In an earplug that applicant has constructed and tested, and which is identified as QBIHYG in Table I; the shell has a length A of 0.8 to 0.875 inch, or a length of about 0.84 inch. Its maximum diameter B (before stem insertion) is 0.61 inch. The maximum diameter C of its front portion at 60 is 0.37 to 0.405 inch, or about 0.39 inch. The neck part is cylindrical with a diameter D of 0.15 inch, and a length F of 0.10 inch which is at least 10 percent of the entire body length. The tapered passage part 54 is tapered at an angle G of 30°, and is preferably at least 20°, with the diameter H at the front end of the taper being about 0.21 inch. The average thickness of the shell walls is about 0.06 inch, which is the thickness at the shell front end 30. The angles P and Q are respectively 7° and 45°.

The stem 16 includes a shaft 72 having a diameter J of 0.146 inch, and which is very closely slideable within the shell passage neck part 42 (to block noise and provide stability). The front flange (32) has a diameter K of 0.25 inch. Its front surface 74 is tapered to face forwardly and away from the axis, at a taper angle V of about 30°. The rear surface 76 is substantially untapered as seen in the side elevation view of FIG. 3. The rear flange 34 has a diameter L of 0.376 inch. The space M between flanges is 0.28 inch, and was designed so that when the forward flange engaged the front end of the tapered passage portion 54, the rear flange 34 was in slight interference fit with the shell rear portion 22.

shell passage is of greater diameter both forward and rearward of such neck part. The stem has a forward flange that lies forward of the neck part, and which helps pull the shell out of an ear canal when the stem is pulled out. The stem preferably has a rear flange which lies rearward of the passage neck part, and which has a diameter that is at least 80 percent of the diameter of the largest location at the forward portion of the shell, with the rear flange stabilizing the stem in the shell, and providing the added unexpected benefit of blocking substantial additional noise.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. An earplug comprising:
   a body of soft resilient material in the form of a shell having a shell forward portion that has a closed front end and that is constructed to enter the ear canal of a person, and having a shell rear portion for lying at least partially outside the ear canal, said shell having a shell passage extending in lengthwise forward and rearward directions through said shell rear portion and along most of the length of said shell forward portion;
   a stem extending along most of the length of said passage and having a stem front end, said stem lying in an initial position wherein said stem front end lies substantially against said shell closed front end, with said shell front end being forwardly elongatable and with said stem being forwardly slidable in said shell from said initial position so when said stem is pushed forward, said stem front end forwardly elongates said shell front end;

said shell passage having a neck part at a rear of said shell forward portion, with said neck part forming an opening of a first diameter and with said shell passage having a diameter greater than said first diameter immediately forward of said opening, and said stem having a forward flange lying at a forward flange-engaging location along said shell passage which is forward of said neck part, with said forward flange having a greater diameter than said first diameter of said opening of said neck part.

2. The earplug described in claim 1 wherein:

said shell rear portion has a second flange-engaging location;

said stem has a rear flange which lies at said second flange-engaging location and which has about the same diameter as said shell rear portion at said rear flange-engaging location and which is forwardly shiftable along said shell rear portion.

3. The earplug described in claim 2 wherein:

both said forward flange and said rear flange lie in interference fit with said shell in said initial position of said stem, but said shell being of sufficiently resilient material to allow said stem to shift forwardly from its initial position.

4. The earplug described in claim 1 wherein:

said shell rear portion has a flange-engaging location, and said stem has a rear flange that engages said stem-engaging location;

said second flange-engaging location is spaced rearward of said neck and there is an unoccupied space between said stem and said shell rear portion, between said neck and said second flange-engaging location, into which said rear flange can shift when said stem is slid forward.

5. An earplug comprising:

a body of elastomeric material in the form of a shell with a closed forward end and with an open rear end, said shell forming a shell passage that extends from said open rear end to a passage forward end, said shell passage having a necked part lying about halfway along the length of said shell, with said shell passage having a larger diameter both forward and rearward of said necked part than at said necked part;

a stem lying in said shell passage, said stem having a cylindrical shaft of about the same diameter as said passage necked part and extending through said necked part of said passage, said stem having forward and rearward flanges with said forward flange lying in interference fit with said shell at a location forward of said necked part, and with said rearward flange lying rearward of said necked part and substatially in contact with said shell.

6. The earplug described in claim 5 wherein:

said shell passage has an enlarged passage part lying forward of said necked part and having a greater diameter than said necked part, and said passage has a tapered part lying between said enlarged part and said necked part, with said tapered part being tapered at an angle of at least 20°, and with said front flange engaging said shell at about the front end of said tapered part.

7. The earplug described in claim 5 wherein:

said necked part is of cylindrical shape and has a length that is at least 10 percent of the entire length of said earplug body.

8. The earplug described in claim 5 including:

a head band of a size to fit halfway about a person's head, with each end of said band having a projection with an enlarged forward head, and with said stem having a rear end with a rearwardly-opening stem passage for receiving one of said projections, said stem passage having an undercut for receiving said enlarged head, and with said stem being formed of elastomeric material so said head can be forced into said stem passage.

9. The earplug described in claim 5 wherein:

said body has a forward portion of an outside diameter of about 0.4 inch to comfortably fit into a person's ear canal, and has a rearwardly-flared rear portion for lying at least partially outside a person's ear canal;

the diameter of said rearward flange of said stem is at least about as great as the outside diameter of said body forward portion, whereby the rearward flange can block noise.

* * * * *